United States Patent [19]
Bitonti et al.

[11] Patent Number: 5,681,863
[45] Date of Patent: Oct. 28, 1997

[54] NON-METABOLIZABLE CLOMIPHENE ANALOGS FOR TREATMENT OF TAMOXIFEN-RESISTANT TUMORS

[75] Inventors: Alan J. Bitonti, Maineville; Russell J. Baumann, Cincinnati, both of Ohio

[73] Assignee: Merrell Pharmaceuticals Inc., Cincinnati, Ohio

[21] Appl. No.: 350,192

[22] Filed: Dec. 5, 1994

Related U.S. Application Data

[62] Division of Ser. No. 196,817, Feb. 10, 1994, Pat. No. 5,410,080, which is a continuation of Ser. No. 945,305, Sep. 15, 1992, abandoned.

[51] Int. Cl.$^6$ ................................................. A61K 31/135
[52] U.S. Cl. ................................................. 514/648; 514/649
[58] Field of Search ............................. 514/648, 649

[56] References Cited

U.S. PATENT DOCUMENTS

| | | | |
|---|---|---|---|
| 2,750,416 | 6/1956 | Exner et al. | 260/570.9 |
| 3,143,568 | 8/1964 | Cavalini et al. | 260/518 |
| 3,244,705 | 4/1966 | Palopoli et al. | 260/247 |
| 3,631,109 | 12/1971 | O'Sega et al. | 260/570.9 |
| 4,696,949 | 9/1987 | Toivola et al. | 514/644 |
| 4,839,155 | 6/1989 | McCague | 514/651 |
| 5,114,951 | 5/1992 | King et al. | 514/290 |
| 5,130,424 | 7/1992 | Weintraub | 540/28 |

*Primary Examiner*—Jerome D. Goldberg
*Attorney, Agent, or Firm*—Nelsen L. Lentz

[57] ABSTRACT

Compounds of the formula:

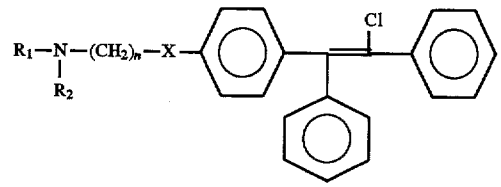

wherein $R_1$ and $R_2$ are each selected from the group consisting of $C_1$–$C_2$ lower alkyl; X is NH or S; and n is a whole number within the range of 1–4 inclusive; and when n=0, X is $(CH_2)_3$ and the pharmaceutically acceptable salts thereof have been shown to be effective in treating tamoxifen resistant tumors.

4 Claims, No Drawings

NON-METABOLIZABLE CLOMIPHENE ANALOGS FOR TREATMENT OF TAMOXIFEN-RESISTANT TUMORS

This is a division of application Ser. No. 08/196,817, filed Feb. 10, 1994 now U.S. Pat. No. 5,410,080, which was a continuation of Ser. No. 07/945,305, filed Sep. 15, 1992, now abandoned, which is herein incorporated by reference.

BACKGROUND OF THE INVENTION

This application relates to non-metabolizable analogs of clomiphene which have been shown to be effective in reducing the proliferation of cell lines known to be resistant to tamoxifen, a known anti-tumor agent. Two of the compounds specifically demonstrated to be useful according to the claimed invention have been disclosed previously. Murphy and Sutherland in the *Journal of Clinical Endocrinology and Metabolism*, 57(2), 373, disclose that compounds of this invention were also effective in inhibiting the growth of MCF-7 cells, a cell line sensitive to tamoxifen. In CA:64 8081d, a method of preparing 3-[p-(2-chloro-1,2-diphenylvinyl)phenyl]-N,N-diethyl-hydrochloride was disclosed. At that time the compound was alleged to be useful in the treatment of gynecological defects and hypercholesterolemia. In CA:63 535h, the same compound is presented and its use as an inhibitor of pituitary gonadotropin was disclosed.

SUMMARY OF THE INVENTION

Specifically, this application relates to a method of treating tamoxifen-resistant tumors which comprises administering to a patient in need of such treatment an effective amount of a compound of the formula:

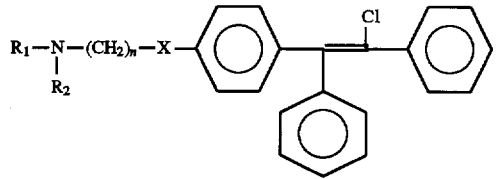

wherein $R_1$ and $R_2$ are each selected from the group of $C_1$–$C_4$ lower alkyl; X is NH or S; and n is a whole number within the range of 1–4, inclusive; and when n=0, X is $(CH_2)_3$ and the pharmaceutically acceptable salts thereof.

DETAILED DESCRIPTION OF THE INVENTION

As used herein the term "$C_1$–$C_4$" refers to a saturated straight or branched chain hydrocarbon radical of one to four carbon atoms. Included within the scope of this term are methyl, ethyl, n-propyl, isopropyl, n-butyl, isobutyl and the like.

The compounds of the present invention can be prepared as described in Schemes A, and B. All the substituents, unless otherwise indicated, are previously defined. The reagents and starting materials are readily available to one of ordinary skill in the art.

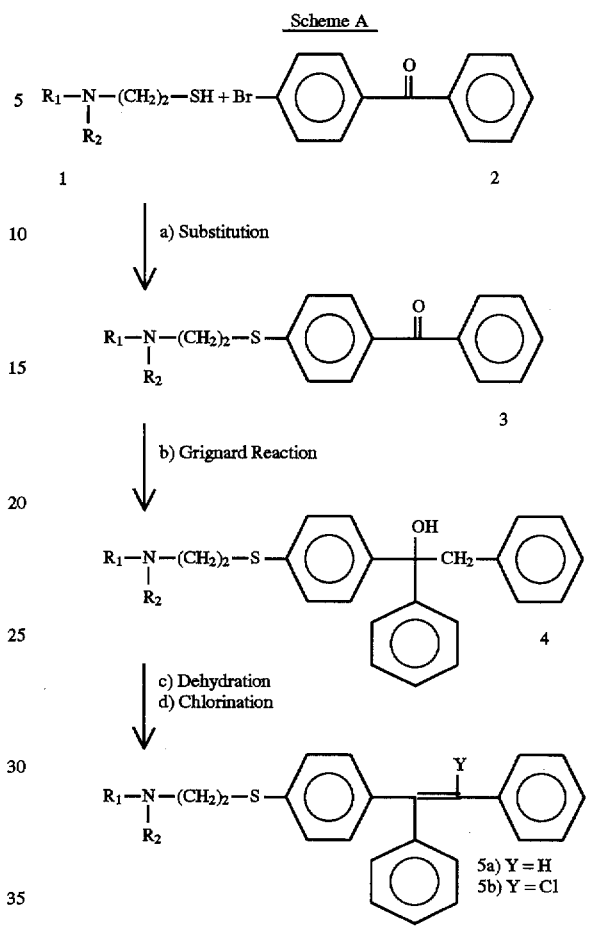

In step a, 4-bromobenzophenone (2) is added to the anion of the appropriately substituted 2-dialkylaminoethanethiol (1) to provide the substitution product described by structure (3).

For example, 2-diethylaminoethanethiol hydrochloride is treated with two equivalents of a suitable base, such as sodium methoxide in a suitable solvent such as ethanol to produce the anion. To this is added an equivalent of 4-bromobenzophenone and a catalytic amount of cupric oxide. The reaction is heated to reflux for about 24 hours. The solvent is then removed under vacuum and the residue purified by techniques well known to one skilled in the art. For example, dissolve the residue in an organic solvent such as ether, rinse with water, dry over a suitable drying agent, such as anhydrous magnesium sulfate filter and concentrate under vacuum. Purify the residue by column chromatography using a suitable eluent such as light petroleum ether on a suitable stationary phase such as alumina to provide the purified substitution product described by structure (3).

In step b, the substitution product described by structure (3) is treated with an appropriate Grignard reagent to provide the alcohol described by structure (4).

For example, an appropriate Grignard reagent such as benzylmagnesium chloride is added to the substitution product described by structure (3) in a suitable organic solvent, such as ether and heated to reflux for about 3 hours. The reaction is then quenched by pouring into saturated ammonium chloride. The product is recovered from the reaction by extractive methods and purified by recrystallization techniques well known to one skilled in the art to provide the alcohol described by structure (4).

In step c, the alcohol described by structure (4) is dehydrated under acidic conditions to provide the olefin described by structure (5a).

For example, the alcohol described by structure (4) is treated with a suitable acid, such as 10% hydrochloric acid in a suitable organic solvent, such as ethanol and heated on a steam bath for about 4 hours. The reaction is then made basic with a suitable base, such as 40% sodium hydroxide. The product is recovered from the reaction by extractive methods well known to one skilled in the art to provide the olefin described by structure (5a).

In step d, the olefin described by structure (5a) is chlorinated by treatment with chlorine to provide the vinylchloride described by structure (5b).

For example, the olefin described by structure (5a) is dissolved in a suitable organic solvent, such as chloroform and treated with an excess of chlorine dissolved in a suitable organic solvent such as ether. The reaction is stirred at room temperature for about 2 hours and refluxed for about 2 hours. The solvent is then removed under vacuum, the residue is dissolved in hot ethyl acetate, cooled and filtered. The filtrate is concentrated under vacuum and the residue is converted to the free base by treatment with a suitable base, such as 10% sodium hydroxide. The free base is extracted into a suitable organic solvent, such as ether and then converted to the citrate salt by techniques well known to one skilled in the art to provide the vinylchloride described by structure (5b).

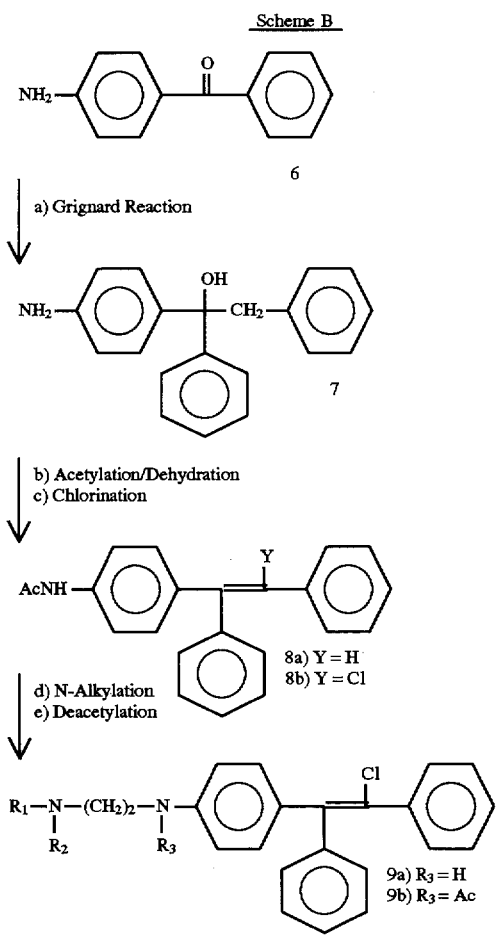

In step a, the 4-aminobenzophenone (6) is treated with an appropriate Grignard reagent to provide the alcohol described by structure (7).

For example, the 4-aminobenzophenone (6) is dissolved in a suitable organic solvent, such as ether and an excess of an appropriate Grignard reagent, such as benzylmagnesium chloride in ether is slowly added to the solution. The reaction is allowed to stir for about 18–24 hours and then it is poured into ice cold saturated ammonium chloride. The product is isolated by extractive methods and purified by recrystallization techniques which are well known to those skilled in the art to provide the alcohol described by structure (7).

In step b, the alcohol described by structure (7) is concomitantly acetylated and dehydrated by treatment with acetic anhydride to provide the olefin described by structure (8a).

For example, the alcohol described by structure (7) is dissolved in a suitable organic solvent such as pyridine. An excess of acetic anhydride is slowly added to the reaction which is then heated on a steam bath for about 18–24 hours. After cooling, the solvent is removed under vacuum and the residue is purified by extractive methods well known to one skilled in the art to provide the olefin described by structure (8a).

In step c, the olefin described by structure (8a) is chlorinated by treatment with chlorine to provide the vinylchloride described by structure (8b).

For example, the olefin described by structure (8a) is dissolved in acetic acid and an excess of chlorine dissolved in carbon tetrachloride is slowly added to the solution. The reaction is stirred at room temperature for about 1 hour and then heated on a steam bath for about 2 hours. After cooling, the solvent is removed under vacuum and the residue is purified by recrystallization techniques well known to one skilled in the art to provide the vinylchloride described by structure (8b).

In step d, the vinylchloride described by structure (8b) is N-alkylated by treatment with an appropriately substituted 2-dialkylaminoethyl chloride hydrochloride in the presence of base to provide the N-alkylated vinylchloride described by structure (9a).

For example, the vinylchloride described by structure (8b) is combined with a slight excess of 2-diethylaminoethyl chloride hydrochloride and an excess of a suitable base, such as potassium hydroxide, in a suitable organic solvent such as acetone. The reaction is refluxed for about 2 hours with stirring. The reaction is then filtered, concentrated under vacuum and the residue is purified by extractive methods well known to one skilled in the art to provide the N-alkylated vinylchloride described by structure (9a).

In step e, the N-alkylated vinylchloride described by structure (9a) is deacetylated by treatment with acid to provide the deacetylated vinylchloride described by structure (9b).

For example, the N-alkylated vinylchloride described by structure (9a) is treated with an excess of a suitable acid, such as 10% hydrochloric acid and heated on a steam bath for about 6 hours. After cooling, the reaction is treated with a suitable base, such as 10% sodium hydroxide until the reaction is basic. The product is isolated by extractive methods well known to one skilled in the art. It is then converted to the citrate salt by treatment with citric acid and purified by recrystallization techniques well known to one skilled in art to provide the citrate salt of the deacetylated vinylchloride described by structure (9b).

The following examples present typical syntheses as described by Schemes A and B. These examples are understood to be illustrative only and are not intended to limit the scope of the invention in any way. As used in the following examples, the following terms have the meanings indicated: "g" refers to grams, "mol" refers to moles, "mmol" refers to millimoles, "mL" refers to milliliters, "°C." refers to degrees Celsius, and "mg" refers to milligrams.

EXAMPLE 1

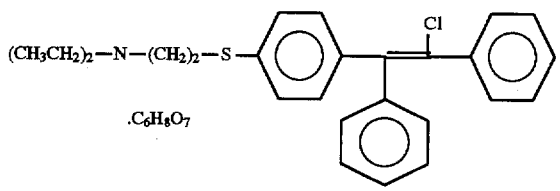

2-[p-(2-Chloro-1,2-diphenylvinyl)-phenylthio] triethylamine Dihydrogen Citrate

Scheme A, step a; Combine 2-diethylaminoethanethiol hydrochloride (65.5 g, 0.39 mol) and sodium methoxide (42.1 g, 0.78 mol) in ethanol (1 L). Reflux for 15 minutes. Then add 4-bromobenzophenone (100 g, 0.38 mol) and cupric oxide (1 g). Reflux for 24 hours. Remove the solvent under vacuum and dissolve the residue in ether and water. Separate the ether layer and extract with 5% hydrochloric acid. Treat the acidic extract with sodium hydroxide until it becomes basic. Then extract the basic aqueous layer with ether. Dry the ether extract over anyhydrous magnesium sulfate, treat with charcoal, filter and concentrate under vacuum. Purify the residue by column chromatography (light petroleum ether on alumina) to provide the substituted benzophenone of structure (3) in which $R_1$ and $R_2$ are ethyl groups (80 g, 67%).

Scheme A, step b; Add benzylmagnesium chloride (0.2 mol in ether) to the above prepared substituted benzophenone (3) (31.3 g, 0.1 mol) in ether and reflux for 3 hours. After cooling, cautiously treat the reaction with saturated ammonium chloride. Separate the layers, dry the organic phase over anhydrous magnesium sulfate, treat with charcoal, filter and concentrate under vacuum. Recrystallize twice from low petroleum ether to provide the alcohol of structure (4) in which $R_1$ and $R_2$ are ethyl groups (31 g, 76%), mp 60°–62° C.

Scheme A, step c; Combine alcohol (4) (26 g, 0.064 mol) with 10% hydrochloric acid (250 mL) and ethanol (100 mL). Heat the reaction on a steam bath for 4 hours in an open flask. All the ethanol will evaporate. Treat the reation with 40% sodium hydroxide under it becomes basic. Extract the basic aqueous phase with ether. Dry the ether extract over anhydrous magnesium sulfate, filter and concentrate under vacuum to provide the olefin of structure (5a) in which $R_1$ and $R_2$ are ethyl groups (25 g, 100%).

Scheme A, step d; Dissolve the olefin described by structure (5a) (25 g) in chloroform (500 mL) and treat with chlorine (150 mL of 0.53M solution in ether). Stir for 2 hours and then reflux for 2 hours. Add an additional amount of chlorine (150 mL of 0.53M solution in ether) and reflux untill GLC indicates no starting material remains. Remove the solvent under vacuum and dissolve the residue with hot ethyl acetate. After cooling, filter the solution and concentrate the filtrate under vacuum. Convert the residue to the free base by treatment with 10% sodium hydroxide and ether. Separate the layers and dry the organic phase over anhydrous magnesium sulfate, filter and concentrate under vacuum. Treat the residue with citric acid (12.8 g) in a small amount of butanone and collect the solid. Recrystallize this twice from butanone/ethyl acetate (1:1). Again convert this to the free base as performed above and purify the free base by chromatography (10% methylene chloride/high petroleum ether, alumina). Treat the purified free base with citric acid (2.3 g) in butanone and collect the solid. Recrystallize from butanone to provide the title compound of structure (5b) (5.5 g), mp 107°–112° C. dec.

Anal. Calcd for $C_{26}H_{28}ClNS \cdot C_6H_8O_7$: C, 62.58, H, 5.91, N, 2.28. Found: C, 62.54, H, 6.06, N, 2.19.

EXAMPLE 2

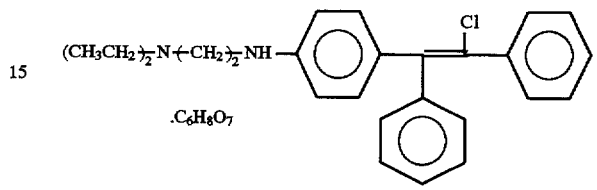

2-[p-(2-Chloro-1,2-diphenylvinyl)-anilino] triethylamine Dihydrogen Citrate

Scheme B, step a; Suspend 4-aminobenzophenone (6) (50 g, 0.25 mol) in ether (500 mL) and slowly add benzylmagnesium chloride (1 L of a 1M solution in ether) over 1.5 hours. Allow the reaction to stir overnight. Cautiously pour the reaction onto ice and ammonium chloride. Separate the layers, wash the organic phase with water, dry over anhydrous magnesium sulfate, filter and concentrate under vacuum. Dissolve the residue in hot isopropanol. After cooling, collect the solid to provide the alcohol of structure (7) (47 g, 64%), mp 104°–106° C.

Scheme B, step b; Combine the above prepared alcohol (7) (40 g, 0.138 mol) and pyridine (75 mL). Slowly add acetic anhydride (50 mL) to the reaction and heat on a steam bath overnight. After cooling, remove the solvent under vacuum, dissolve the residue in ether and wash with water. Dry the organic phase over anhydrous magnesium sulfate, filter and concentrate to provide the olefin of structure (8a) (47 g).

Scheme B, step c; Dissolve the above prepared olefin (8a) in acetic acid (250 mL) and slowly add chlorine (350 mL of a 0.46M solution in carbon tetrachloride) to the solution. After addition, stir the reaction at room temperature for 1 hour and then heat on a steam bath for 2 hours. After cooling, concentrate under vacuum. Purify by recrystallization from 95% ethanol to provide the vinylchloride of structure (8b), (14.8 g), mp 189°–191° C.

Scheme B, step d; Combine the above prepared vinylchloride (8b) (17.4 g, 0.05 mol), 2-diethylaminoethyl chloride hydrochloride (10 g, 0.058 mol) and powdered potassium hydroxide (6.7 g, 0.12 mol) in acetone (150 mL). Reflux for 2 hours with stirring. Filter the reaction and concentrate on a steam bath. Dissolve the residue in ether and water. Separate the layers and wash the organic phase with water, dry over anhydrous magnesium sulfate, filter and concentrate under vacuum to provide the N-alkylated vinylchloride of structure (9a) in which $R_1$ and $R_2$ are ethyl groups (14 g, 67%).

Scheme B, step e; Dissolve the above prepared N-alkylated vinylchloride compound (9a) in 10% hydrochloric acid (200 mL) add concentrated hydrochloric acid (10 mL) and heat on a steam bath for 6 hours. Allow the reaction to sit at room temperature overnight and then treat with 10% sodium hydroxide until the solution becomes basic. Extract the basic solution with ether. Wash the organic phase with water, dry over anhydrous magnesium sulfate, filter and concentrate under vacuum. Treat the residue with citric acid (4.3 g) in butanone to provide 12 g of crude material. Recrystallize twice from butanone to provide the title compound of structure (9b) (7.2 g), mp 121°–125° C.

Anal. Calcd for $C_{26}H_{29}ClN_2 \cdot C_6H_8O_7$: C, 64.36, H, 6.25, Cl, 5.94. Found: C, 64.68, H, 6.27, Cl, 6.14.

ANTIPROLIFERATION OF HUMAN BREAST CANCER CELLS BY TRIPHENYLETHYLENES

Breast Cancer Cells

MCF-7; A Cell line sensitive to the antiestrogen, tamoxifen.

LY-2: A variant of MCF-7 resistant to tamoxifen.

Antiproliferation test Procedure:

The tests were conducted in 96-well microtiter plates. $5 \times 10^3$ cells were added to each well. Culture medium and drug solutions were added to wells with a Perkin Elmer Cetus PRO/PETTE. The culture medium was IMEM supplemented with 5% fetal bovine serum. Eight drug concentrations were tested, in duplicate, from 0.078 micromolar (µM) to 10 µM. After four days incubation the medium was replaced with fresh medium containing drug, and after a total of seven days, the cell monolayers were fixed with trichloracetic acid and stained with sulforhodamine dye. Absorbances (492 nm) of the extracted dye solutions were measured with a Titertek Multiscan plate reader. Dose response curves (percent of control absorbances vs. drug concentrations) were constructed in order to estimate $IC_{50}$ values defined as the drug concentrations (micromolar) which inhibited 50% profileration. As shown in Table 1, the $IC_{50}$ values of MDL-6866F, MDL-10007F AND MDL-10222F were lower than the $IC_{50}$ values of tamoxifen against the profileration of both cell lines.

MDL-6866F, MDL-10007-F and MDL-10222F are compounds within the scope of this invention. MDL-1022F is 2-[p-(2chloro-1,2-diphenylvinyl)anilino]triethylamine dihydrogenatrate. MDL-10007F is 2-[p-(2-chloro-1,2-diphenylvinyl)phenylthio]thiethylamine dihydrogen citrate. MDL-6866F is 1-[p-γ-diethylaminopropyl)phenyl]-1,2-diphenylchloroethylene dihydrogen citrate.

TABLE 1

TRIPHENYLETHYLENE $IC_{50}$, AGAINST BREAST CANCER CELLS

| Triphenylethylene | $IC_{50}$ (µM) Cell line | |
|---|---|---|
| | MCF-7 | LY2 |
| MDL 6866F | 0.32 | 1.6 |
| MDL 10007F | 0.37 | 1.0 |
| MDL 10222F | 0.70 | 3.8 |
| TAMOXIFEN | 1.7 | 8 |

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically a protective amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of this invention can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

What is claimed is:

1. A method of treating tamoxifen-resistant tumors which comprises administering to a patient in need of such treatment an effective amount of 2-[p-(2-Chloro-1,2-diphenylvinyl)-anilino]triethylamine or the pharmaceutically acceptable salts thereof.

2. A method of treating tamoxifen-resistant tumors which comprises administering to a patient in need of such treatment an effective amount of 2-[p-(2-Chloro-1,2-diphenylvinyl)-phenylthio]triethylamine or the pharmaceutically acceptable salts thereof.

3. A method of treating tamoxifen-resistant tumors which comprises administering to a patient in need of such treatment an effective amount of 1-[p-γ-diethylaminopropyl)-phenyl]-1,2-diphenylchloroethylene or the pharmaceutically acceptable salts thereof.

4. A method as in claims 1, 2 or 3 wherein the pharmaceutically acceptable salt is dihydrogen citrate.

\* \* \* \* \*